US009040503B2

(12) United States Patent
Jin et al.

(10) Patent No.: US 9,040,503 B2
(45) Date of Patent: May 26, 2015

(54) MEDICINAL CARBOHYDRATES FOR TREATMENT OF RESPIRATORY CONDITIONS

(75) Inventors: Betty Jin, Mount Waverley (AU); Paul Arthur Jones, Balwyn (AU); Ee Ling Seah, Lysterfield South (AU); Wen Yang Wu, Mount Waverley (AU); Peter James Jenkins, Prahran East (AU)

(73) Assignee: Australian Biomedical Company Pty Ltd., Mount Waverly (AU)

(*) Notice: Subject to any disclaimer, the term of this patent is extended or adjusted under 35 U.S.C. 154(b) by 35 days.

(21) Appl. No.: 13/380,219

(22) PCT Filed: Jul. 2, 2010

(86) PCT No.: PCT/AU2010/000846
§ 371 (c)(1),
(2), (4) Date: Feb. 21, 2012

(87) PCT Pub. No.: WO2011/000053
PCT Pub. Date: Jan. 6, 2011

(65) Prior Publication Data
US 2012/0142619 A1    Jun. 7, 2012

(30) Foreign Application Priority Data
Jul. 3, 2009    (AU) .................... 2009903123

(51) Int. Cl.
*A61K 31/70* (2006.01)
*A61K 31/7008* (2006.01)
*A61K 31/7012* (2006.01)

(52) U.S. Cl.
CPC ......... *A61K 31/7008* (2013.01); *A61K 31/7012* (2013.01)

(58) Field of Classification Search
CPC ........... A61K 31/7008; A61K 31/7012; A61K 31/7028; A61K 31/7068
USPC ........................................................ 514/62
See application file for complete search history.

(56) References Cited

U.S. PATENT DOCUMENTS

| 5,834,423 | A | 11/1998 | Koketsu et al. |
| 6,274,568 | B1 | 8/2001 | Schnaar et al. |
| 7,157,431 | B2 * | 1/2007 | McAnalley et al. ............ 514/23 |
| 2002/0022601 | A1 | 2/2002 | Konno et al. |
| 2006/0193824 | A1 | 8/2006 | Rubin et al. |
| 2007/0042995 | A1 | 2/2007 | Xu et al. |
| 2007/0259094 | A1 | 11/2007 | Wassenaar |
| 2009/0209488 | A1 | 8/2009 | Brown |

FOREIGN PATENT DOCUMENTS

| CA | 2155910 | 2/1997 |
| CN | 1156026 A | 8/1997 |
| EP | 0429430 | 5/1991 |
| EP | 1609473 | 12/2005 |
| EP | 2060257 | 5/2009 |
| JP | 1990-177891 | 7/1990 |
| JP | 198668418 | 6/1991 |
| JP | 03-206050 | 9/1999 |
| JP | 2001131074 A | 5/2001 |
| JP | 2006-521299 | 9/2006 |
| JP | 2008273919 A | 11/2008 |
| RU | 94034735 | 7/1996 |
| WO | WO02/101071 | 12/2002 |
| WO | WO-2006/127977 | 11/2006 |
| WO | WO2006/127977 | 11/2006 |
| WO | WO2009/020641 | 2/2009 |

OTHER PUBLICATIONS

XP-002694489 Database WPI; Week 200137; Thomas Scientific London, GB; AN 2001-344214 and CN 1156026 (Aug. 6, 1997).
Keppler et al. "UDP-GlcNAc 2-epimerase: A regulator of cell surface sialylation"; Science; 284:5418(1372-1376) (May 21, 1999).
XP-002694542 Database WPI; Week 199710; Thomas Scientific, London, GB; An 1997-103654 and JP 8337532 (Dec. 24, 1996).
Dosanjh A et al "Expression of DELTAF508 Cystic Fibrosis Transmembrane Regular (CFTR) Decreases Membrane Sialylation", The Open Respiratory Medicine Journal, vol. 3, 2009, pp. 79-84.
"Cell Survival" retrieved from http://www.ncbi.nlm.nih.gov/mesh68002470.
Nakano et al.; "Sialic acid in human milk: composition and functions"; Acta Paediatrica Taiwanica; 42(1):11-17(2001).
Van Alphen et al.; "Blocking of fimbria-mediated adherence of haemophilus influenzae by sialyl gangliosides"; Infection and Immunity; 59(12):4473-4477 (1991).
Schroten et al. "Binding of cloned s-fimbriated *E. coli* to human buccal epithelial cells-difference inhibition of binding by neonatal saliva and adult saliva"; Zentralblatt fur Bakteriologie; 274:514-518 (1991).
Schroten et al.; "Fab-independent antiadhesion effects of secretory immunoglobulin A on S-fimbriated *Escherichia coli* are mediated by sialyloligosaccharides"; Infection and Immunity; 66(8):3971-3793 (1998).
Arcasoy et al.; "MUC1 and other sialoglycoconjugates inhibit adenovirus-mediated gene transfer to epithelial cells"; American Journal of Respiratory Cell and Molecular Biology; 17(4):422-435 (1997).
Schulte et al.; "Histochemical methods for characterizing secretory and cell surface sialoglycoconjugates"; The Journal of Histochemistry and Cytochemistry; 33(5):427-438 (1985).
Ruhl et al.; "Identification of polymorphonuclear leukocyte and HL-60 cell receptors for adhesins of *Streptococcus gordonii* and actinomyces naeslundii"; Infection and Immunity; 68(11):6346-6354, 2000.
Dosanjh et al.; "Expression of ΔF508 cystic fibrosis transmembrane regulator (CFTR) decreases membrane sialylation"; The Open Respiratory Medicine Journal; 3:79-84 (2009).
Berkow, et al., "The Merck Manual of Diagnosis and Therapy", Merck Research Laboratories, 1992 (Translation of relevant parts).
Peltola, et al., "Respiratory viruses predisposing to bacterial infections: role of neuraminidase", Pediatr. Infect. Dis. J, 2004.

* cited by examiner

*Primary Examiner* — Elli Peselev
(74) *Attorney, Agent, or Firm* — Cesari and McKenna, LLP

(57) ABSTRACT

A method of promoting recovery of cell viability of a damaged respiratory cell. The method includes a step of administering to the cell at least one pharmaceutically acceptable compound, which accelerates sialyglycoconjugate biosynthesis to restore sialylglycoconjugates on the surface of the respiratory cell. Also disclosed are a method and a pharmaceutical composition, both for treating a respiratory condition.

8 Claims, 1 Drawing Sheet

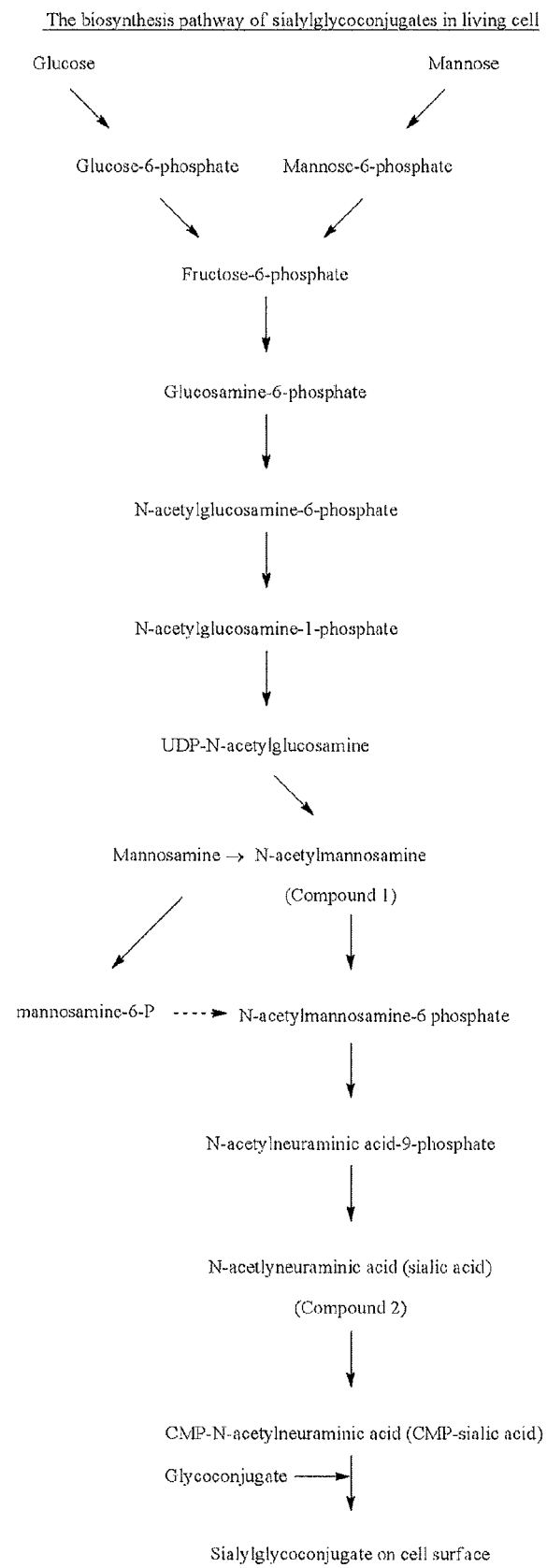

MEDICINAL CARBOHYDRATES FOR TREATMENT OF RESPIRATORY CONDITIONS

CROSS-REFERENCE TO RELATED APPLICATIONS

This application is the National Stage of International Application No. PCT/AU2010/000846, filed on Jul. 2, 2010, which claims the priority of Australian Application No. 2009903123, filed on Jul. 3, 2009. The contents of both applications are hereby incorporated by reference in their entirety.

FIELD OF THE INVENTION

This invention is related to a novel method and a group of carbohydrates of Formula (1) and/or (2), and their compositions for treating cough and related respiratory conditions including post viral/bacterial infections, acute/chronic bronchitis, COPD, and inflammatory conditions.

BACKGROUND OF THE INVENTION

In humans, the respiratory tract, with an area of a football field is the largest surface connecting the body with the outside world required for sufficient exchange of air; meanwhile, it is affected by many physical, chemical, and biological substances in the air to cause disorders including asthma, chronic obstructive pulmonary disease, inflammatory conditions of the lung and respiratory tract. Also, some genetic disorders such as cystic fibrosis are affected by the respiratory tract's connection with the outside world. Viruses and bacteria may enter the body and cause infections in the respiratory tract to occur.

Cough is one of the common conditions that needs to be treated. However, the currently available treatments are only limited in symptom relief leaving the body to recover by itself and in many cases the recoveries are sluggish.

In Australia, the sale of cough syrup is over $20 million a year. It is estimated that the worldwide market of cough syrup exceeds $1 billion per annum.

Persistent cough sometimes with period of normality lasting for months or even years is attributed to bronchial asthma, occult reflex, or post viral/bacterial infections and smoking causing the airway to become hypersensitive/hyperreactive. Accordingly there is a need for an efficient treatment that can assist the body to recover after it has been affected by many physical, chemical, and biological substances in the air that can cause disorders in the respiratory system.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

The present invention provides in one aspect of the invention a method of promoting restoration of a sialylglycoconjugate on the surface of a damaged respiratory cell of a subject to treat a respiratory condition in the subject, the method including the step of administering to the subject at least one pharmaceutically acceptable compound capable of accelerating sialylglycoconjugate biosynthesis.

In one embodiment, the method provides a recovery of viability of the cell such that the cell is in a better condition for normal biological function to respond to factors which may affect the respiratory surface thereby leading to respiratory conditions such as but not limited coughs, post viral or bacterial infections, acute/chronic bronchitis, chronic obstructive pulmonary disease (COPD), cystic fibrosis and other respiratory inflammatory conditions.

In another embodiment, the present invention provides for the use of a compound selected from the group consisting of compounds of Formula (1) and Formula (2) and their pharmaceutically acceptable salts and derivatives and combinations thereof. The use is for the treatment or prevention of a respiratory condition as herein described.

In other aspects of the invention there are provided compositions and pharmaceutical compositions comprising at least one pharmaceutically acceptable compound capable of accelerating sialylglycoconjugate biosynthesis for use in the treatment and prevention of respiratory conditions.

In yet another aspect of the invention there is provided a method of screening for a compound for the treatment of a respiratory condition, said method comprising:

- subjecting a cell having reduced sialylglycoconjugates on a surface of the cell to a test compound; and
- measuring recovery of sialylglycoconjugates on the surface of the cell after exposure of the test compound to the cell.

Measurement of the recovery of sialylglycoconjugates on the surface of the cell can be determined by a measurement of the viability of the cell.

In yet another aspect of the invention there is provided a method of treating or preventing a respiratory condition in a subject, the method including the step of administering to the subject at least one compound identified by the screening method.

BRIEF DESCRIPTION OF THE FIGURES

FIG. 1 shows the biosynthesis pathway of sialylglycoconjugates in living cell.

DETAILED DESCRIPTION OF THE INVENTION

From cell biology and molecular biology point of view, the hypersensitivity/hyperreactivity of the damaged respiratory tract may be caused by their damaged cell surface which then will be susceptible to the stimulation of irritants. For instance, applicants have found that the respiratory tract cells after viral or bacterial infection often lost terminal sialic acids on their surface sialylglycoconjugates. As a consequence, the viability of the "naked" cell was reduced. This then trigged an inflammatory response leading to bronchitis and cough. Without being limited by theory, it is postulated that restoration of the sialic acids on the cell surface may repair the respiratory tract damaged by infection or other physical, chemical, biological factors, to eventually cue the bronchitis, and stop the cough.

Applicants have now shown in this application cell culture experiments conducted in two human respiratory tract cell lines: Small Airways Epithelial Cells (SAEC) and Normal Human Bronchial/Tracheal Epithelial Cells (NHBE). The cells were originally treated with neuraminidases (NAs) from influenza virus or bacteria. The NAs cleave the sialic acids from the cell surface sialylglycoconjugates. As a consequence, the viability of the "naked" cells was reduced. For example, SAEC lost more than 25% viability when treated with *C. perfringens* NA at a final concentration of 0.01 U/ml, or with influenza virus NWS/G70C NA at a final concentration of 0.17 µg/well. Similar results were also obtained in the NHBE cell line. After the cells were treated with NA, the cells were washed to remove NA, then incubated with compounds of Formula (1) and/or (2) for 24 hrs. Eventually the cells' viabilities were determined. The results (Examples 7-36) showed that a group of carbohydrates of Formula (1) and/or (2) could help the recovery of the viability of the damaged respiratory tract cells by restoring the sialylglycoconjugates on their surface.

Accordingly, the present invention provides in one aspect of the invention a method of promoting restoration of a sialylglycoconjugate on the surface of a damaged respiratory cell of a subject to treat a respiratory condition in the subject, the method including the step of administering to the subject at least one pharmaceutically acceptable compound capable of accelerating sialylglycoconjugate biosynthesis.

The present invention provides in another aspect of the invention a method of promoting recovery of cell viability of a damaged respiratory cell of a subject to treat a respiratory condition in the subject, the method including the step of administering to the subject at least one pharmaceutically acceptable compound capable of accelerating sialylglycoconjugate biosynthesis.

The promotion of the restoration of a sialylglycoconjugate on the surface of a respiratory cell may also indicate the recovery of the cell to a viable state or recovery of viability such that the cell is in a better condition for normal biological function to respond to factors which may affect the respiratory surface thereby leading to respiratory conditions such as but not limited coughs, post viral or bacterial infections, acute/chronic bronchitis, chronic obstructive pulmonary disease (COPD), cystic fibrosis and other respiratory inflammatory conditions.

In another embodiment, at least one pharmaceutically acceptable compound is selected from the group consisting of carbohydrates capable of participating as intermediates in sialylglycoconjugate biosynthesis, precursors thereof and prodrugs thereof and their pharmaceutically acceptable salts and derivatives and combinations thereof.

The compounds mentioned above may be used orally, by inhalation or injection administration for the treatment of the respiratory conditions selected from the group comprising coughs, post viral or bacterial infections, acute/chronic bronchitis, chronic obstructive pulmonary disease (COPD), cystic fibrosis and other respiratory inflammatory conditions.

Throughout the description and claims of this specification, the word "comprise" and variations of the word, such as "comprising" and "comprises", is not intended to exclude other additives, components, integers or steps.

In another embodiment, the present invention provides for the use of a compound selected from the group consisting of;
compounds of Formula (1):

Formula (1)

Wherein,
When B=H, A could be NHCOCH$_3$, NH$_2$, OH, NH$_2$.HX or when A=H, B could be NHCOCH$_3$, NH$_2$, NH$_2$.HX, HX could be pharmaceutically suitable inorganic or organic acids, such as hydrochloric acid, sulfuric acid, phosphoric acid, acetic acid, citric acid etc;

$R^1$, $R^2$, $R^3$, $R^4$ could be the same or different. They could be H, CH$_3$, (CH$_2$)$_n$CH$_3$ (n=1~20), CH$_2$Ph, COCR$^5$R$^6$R$^7$, CO-active esters, such as piva ester, indenyl ester; $R^5$, $R^6$, $R^7$ could be the same or different. They could be H, CH$_3$, (CH$_2$)$_n$CH$_3$ (n=1~20), C$_6$H$_5$, CH$_2$Ph, CH$_3$CH$_2$(OCH$_2$CH$_2$)$_m$CH$_3$ (m=1~200); and, $R^4$ may be $$\overset{O}{\underset{P}{\|}}\begin{matrix}O-R^{5'}\\O-R^{6'}\end{matrix}$$

$R^{5'}$, $R^{6'}$ could be the same or different. They may be H, or a pharmaceutically suitable inorganic or organic salt, such as, Na, K, Ca, Mg, Zn, NH$_3$, triethylamine etc., or $R^{5'}$, $R^{6'}$ could be a pharmaceutically suitable ester, such as (CH$_2$)$_n$CH$_3$ (n=1~20) or CH$_3$CH$_2$(OCH$_2$CH$_2$)$_m$CH$_3$ (m=1~200) or active ester, such as piva ester, indenyl ester;

and compounds of Formula (2)

Formula (2)

Wherein,
$R^8$ could be H, CH$_3$, (CH$_2$)$_n$CH$_3$ (n=1~20), CH$_2$Ph, COCH$_2$Ph, CO-active ester, such as piva ester, indenyl ester, COCR$^{14}$R$^{15}$R$^{16}$; wherein $R^{14}$, $R^{15}$, $R^{16}$ could be the same or different. They could be H, CH$_3$, (CH$_2$)$_n$CH$_3$ (n=1~20), C$_6$H$_5$, CH$_2$Ph, CH$_3$CH$_2$(OCH$_2$CH$_2$)$_m$CH$_3$ (m=1~200);

$R^8$ may be cytidine, cytidine monophosphate, cytidine diphosphate, cytidine triphosphate, adenosine, adenosine monophosphate, adenosine diphosphate, adenosine triphosphate;

$R^9$ may be H, CH$_3$, pharmaceutically acceptable inorganic or organic salt, such as Na, K, Ca, Mg, Zn, NH$_3$, triethylamine, etc., or a pharmaceutically suitable active ester, such as piva ester, indenyl ester etc., or CH$_2$CR$^{17}$R$^{18}$R$^{19}$ wherein $R^{17}$, $R^{18}$, $R^{19}$ may be the same or different. They could be H, CH$_3$, (CH$_2$)$_n$CH$_3$ (n=1~20), CH$_2$CH$_2$(OCH$_2$CH$_2$)$_m$CH$_3$ (m=1~200), C$_6$H$_5$, CH$_2$Ph;

$R^{10}$, $R^{11}$, $R^{13}$ could be the same or different. They could be H, CH$_3$, (CH$_2$)$_n$CH$_3$ (n=1~20), CH$_2$Ph, active ester, such as piva ester, or COCR$^{20}$R$^{21}$R$^{22}$, wherein $R^{20}$, $R^{21}$, and $R^{22}$ could be the same or different. They could be H, CH$_3$, (CH$_2$)$_n$CH$_3$ (n=1~20), C$_6$H$_5$, CH$_2$Ph, CH$_3$CH$_2$(OCH$_2$CH$_2$)$_m$CH$_3$ (m=1~200);

$$\overset{O}{\underset{P}{\|}}\begin{matrix}O-R^{23}\\O-R^{24}\end{matrix}$$

$R^{23}$, $R^{24}$ could be the same or different. They could be H, CH$_3$, (CH$_2$)$_n$CH$_3$ (n=1~20), CH$_2$CH$_2$(OCH$_2$CH$_2$)$_m$CH$_3$ (m=1~200), CH$_2$Ph, or active ester, such as piva ester, indenyl ester or $CH_2CR^{25}R^{26}R^{27}$, or pharmaceutically acceptable inorganic or organic salt, such as Na, K, Ca, Mg, Zn, $NH_3$, triethylamine etc and $R^{25}$, $R^{26}$, $R^{27}$ may be the same or different. They could be H, $CH_3$, $(CH_2)_nCH_3$ (n=1~20), $C_6H_5$, $CH_2Ph$.

In one embodiment in Formula (1) when A=$NHCOCH_3$, B=H, $R^1$, $R^2$, $R^3$, $R^4$=H, the compound is N-acetyl-D-mannosamine. This will be referred to as Compound (1) throughout this specification.

In another embodiment in Formula (2) when $R^8$, $R^{10}$, $R^{11}$, $R^{12}$, $R^{13}$=H, $R^9$=Na, the compound is N-acetylneuraminic acid sodium salt. (Sialic acid sodium salt). This will be referred to as Compound (2) throughout this specification.

When $R^8$ is cytidine monophosphate, and $R^9$, $R^{10}$, $R^{11}$, $R^{12}$, $R^{13}$=H, the compound is CMP-sialic acid.

Sialic acids as terminal sugars on the oligosaccharide chains of glycoconjugate on the surface of cell are well suited as molecular determinants of specific biological processes such as cellular adhesion [1], formation or masking of recognition determinants[2][3] and stabilization of the structure of glycoproteins[4]. The biosynthesis pathway of sialylglycoconjugates in living cell is shown below in FIG. 1.

It was reported that N-acetylneuraminic acid, but not lactose, dose-dependently protected against the impairment of the mucocilliary transport[6]. Furthermore, pre-treatment with repeated administrations (inhalations) of N-acetylneuraminic acid remarkably prevented the inflammatory changes caused by long term exposure of $SO_2$ in rabbits[7]. It was also reported that oral administration of N-acetyl-D-mannosamine to mammals was rapidly metabolized into glucose[8]. It was also reported that methods of administering N-acetylmannosamine or its derivative (to produce sialic acid in patients who are deficient in the sugar molecule) to treat muscular atrophy including hereditary inclusion body myopathy (HIMB) and distal myopathy with rimmed vacuoles (Nonaka myopathy). Certain kidney conditions such as those arising from hyposialytion of kidney membranes may be treated by this method as well[8b][8c].

However, none of these treatments related to the use of these intermediates for the treatment of respiratory conditions.

Compounds of Formula (1) and/or (2) have been tested for safety by the applicants. For example, Compounds (1) and (2) were used in a tolerance and subchronic toxicity study on Balb-C mice (AEC Approval Code: BAM/B/2005/16). The results for the tolerance study showed that both compounds at 5 g/Kg for oral dose or 2 g/Kg for intraperitoneal dose were well tolerated. In the subchronic toxicity study, the results showed that both compounds at 1 g/Kg/day×30 days for oral dose or 0.5 g/Kg/day×30 days for intraperitoneal dose were non-toxic.

A guinea pig cough model was also established by the applicants. Compounds (1) and (2) were tested in this model. At an oral dose of 500 mg/kg/day×3 days, both compounds could restore the respiratory tract damages caused by neuraminidase in guinea pigs. These in vivo results are in line with the in vitro data. Thus, both the efficacy and safety data support compounds of Formula (1) and/or (2) and particularly compounds (1) and (2) may be useful for medicinal applications.

It has been found by the applicants that the compounds of Formula (1) and/or (2) could speed up the recovery of the viability of damaged respiratory tract cells by restoring sialylglyco-conjugates on their surface.

The compounds of Formula (1) and/or (2) enhance the production of sialylglycoconjugates after entering the cells. Thus, one aspect of this invention relates to the use of compounds of Formula (1) and/or (2), and their pharmaceutically acceptable salts and derivatives and combinations thereof. or their mixtures as active therapeutic agents for the treatment of cough, and related respiratory conditions including post viral/bacterial infections, acute/chronic bronchitis, chronic obstructive pulmonary disease (COPD), cystic fibrosis and inflammatory conditions.

Pharmaceutically acceptable compositions of the compounds of Formula (1) and/or (2) and their mixtures may also be formed by combining them with one or more other active ingredients for the treatment of respiratory conditions. For example, choline theophyllinate (bronchodialator), theophylline (bronchodialator), salbutamol and terbutaline sulfate (relief of bronchospasm associated with asthmas and other respiratory conditions), bromhexine (expectorant, mucolytic), codeine, pholcodeine (analgesic, antitussive), clofedanol (antitussive), pentoxyverine (antitussive), dimethoxanate, glaucine (antitussive), promdate, taloximine, acetyl piperacetamide, eucalypus oil, ammonium chloride, and herbs such as fritillariae cirrhosae (anti-cough herb). Mucin synthesis inhibitors such as talniflumate, 2-amino-phenyl-acetic acids, or combining with some glucocorticoids such as flunisolide (antiasthmatic), or combining with symptom relief pharmaceutically compatible cough syrups, or combining with phosphodiesterase-4 inhibitor, such as cilomilast (Ariflo) for the treatment of chronic obstructive pulmonary disease (COPD).

Furthermore, pharmaceutically acceptable compositions of the compounds of Formula (1) and/or (2) and their pharmaceutically acceptable salts and derivatives and combinations thereof and their mixtures may also be formed by combining them with one or more other active ingredients, for example, antiviral agents such as zanamivir and/or oseltamivir (anti-influenza virus agents), pleconaril and/or enviroxime (anti-rhinovirus agents). antimicrobial agents, such as antibiotics, for example, erythromycins, tetracyclines, rifamycins, penicillins, cephalosporins; quinolones, fluoroquinolones; sulfonamides, and trimethoprims; antifugal agents, such as, amphotericins, clotrimazole, econazole, fluconazole, flucytosine, etc.

References to the compounds of Formula (1) and/or (2) herein include the compounds of Formula (1) and/or (2), and their pharmaceutically acceptable derivatives and salts thereof.

In a further or alternative embodiment there is provided a method for the treatment or prevention of respiratory conditions including post viral/bacterial infections, acute/chronic bronchitis, COPD, cystic fibrosis and inflammatory conditions in animals including humans comprising administering of an effective amount of the compounds of Formula (1) and/or (2).

There is also provided in a further or alternative aspect the use of the compounds of Formula (1) and/or (2) in the manufacture of a medicament for the treatment of respiratory conditions including post viral/bacterial infections, acute/chronic bronchitis, COPD, cystic fibrosis and inflammatory conditions in animals including humans.

The amount of the compounds of Formula (1) and/or (2) required for use in treatment will vary with the route of administration, the nature of the condition being treated and the age and condition of the animal (including human patients), and will ultimately be at the discretion of the attendant veterinarian or physician.

In general a suitable dose will be in the range of from about 0.1 mg to 500 mg/kg of body weight per day, preferably in the range of 0.1 mg to 50 mg/kg/day.

In general, the dosage for oral administration would be 1 mg/kg/day to 500 mg/kg/day, the dose for injection would be 1 mg/kg/day to 100 mg/kg/day. The dose for inhalation would be 0.01 mg/kg/day to 5 mg/kg/day. Preferably, the dose would be 5 mg to 50 mg/kg for oral or injection administration, two to three times a day for 5 to 10 days; the dose would be 0.1 to 0.5 mg/kg for inhalation, one to five times a day for a period of 5 to 10 days.

Treatment is preferably commenced after or at the time the cough or related conditions occur and continues until the cough or related conditions ceased. Suitably treatment is given 1 to 4 times daily and continued for 3 to 30 days.

The desired dose may be presented in a single dose or as divided doses administered at appropriate intervals, for example as two, three, four or more sub-doses per day.

The compounds of Formula (1) and/or (2) are conveniently administered in unit dosage form for example containing 0.1 to 500 mg of active ingredient per unit dosage form. As used herein, the term "unit dose" includes not only individually packaged unit doses such as vials but also aliquots dispensed from vials into syringes and compositions for infusion contained in infusion containers.

While it is possible that, for use in therapy, the compounds of Formula (1) and/or (2) may be administered as the raw chemical, it is preferable to present the active ingredient as a pharmaceutical formulation.

The invention thus further provides a pharmaceutical formulation including the compounds of Formula (1) and/or (2) or a pharmaceutically acceptable derivative thereof together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, or parenteral (including intramuscular, intradermal, sub-cutaneous and intravenous) administration or in a form suitable for administration to the gastrointestinal tract, or in a form suitable for administration to the respiratory tract (including the nasal passages) for example by inhalation or insufflation or for intradermal or sub-cutaneous implantation or for transdermal patch. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous of oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds of Formula (1) and/or (2) may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For rectal administration, unit dose suppositories wherein the carrier is a solid are preferred. Suitable carriers include cocoa butter and other materials commonly used in the art, and the suppositories may be conveniently formed by admixture of the active compound with the softened or melted carrier(s) followed by chilling and shaping in moulds.

For administration to the respiratory tract (including intranasal administration) compounds of Formula (1) and/or (2) may be administered by any of the methods and formulations employed in the art for administration to the respiratory tract.

Thus in general the compounds of Formula (1) and/or (2) may be administered in the form of a solution or a suspension or as a dry powder.

Solutions and suspensions will preferably be aqueous for example prepared from water alone (for example sterile or pyrogen-free water) or water and a physiologically acceptable co-solvent (for example ethanol, propylene glycol, polyethylene glycols such as PEG 400).

Such solutions or suspensions may additionally contain other excipients for example preservatives (such as benzalkonium chloride), solubilising agents/surfactants such as polysorbates (e.g. Tween®80, Span® 80, benzalkonium chloride), buffers, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomizing spray pump.

An aerosol formulation may also be used for the respiratory tract administration, in which the compounds of Formula (1) and/or (2) are provided in a pressurized pack with a suitable propellant such as a chlorofluorocarbon (CFC) for example dichlorodifluoromethane, trichlorofluoromethane or dichlorotetrafluoroethane, carbon dioxide or other suitable gas. The aerosol may conveniently also contain a surfactant such as lecithin. The dose of drug may be controlled by provision of a metered valve.

Alternatively the compounds of Formula (1) and/or (2) may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatin or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronisation.

When desired, formulations adapted to give sustained release of the active ingredient may be employed.

The compounds of Formula (1) and/or (2) may also be used in combination with other therapeutic agents, for example anti-infective agents, such as antibiotics, antiviral agents, and agents for treatment of respiratory conditions. The invention thus provides in a further aspect a combination comprising the compounds of Formula (1) and/or (2) or a pharmaceutically acceptable derivative thereof together with another therapeutically active agent.

The combinations mentioned above may conveniently be presented for use in the form of a pharmaceutical formulation and thus such formulations comprising a combination as defined above together with a pharmaceutically acceptable carrier therefore comprise a further aspect of the invention.

The individual components of such combinations may be administered either sequentially or simultaneously in separate or combined pharmaceutical formulations.

When the compounds of Formula (1) and/or (2) are used with a second therapeutic agent active in therapy, the dose of each compound may either be the same as or differ from that employed when each compound is used alone. Appropriate doses will be readily appreciated by those skilled in the art.

The compounds of Formula (1) and/or (2) and their pharmaceutically acceptable derivatives may be prepared by any methods known in the art for the preparation of compounds of analogous structure.

In another aspect of the invention there is provided a method of screening for a compound for the treatment of a respiratory condition, said method comprising:
 subjecting a cell having reduced sialylglycoconjugates on a surface of the cell to a test compound; and
 measuring recovery of viability of the cell after exposure of the test compound to the cell.

Based on the present invention, other compounds may be used to promote the restoration of a sialylglycoconjugate on the surface of a respiratory cell; or to promote recovery of viability of the cell by its ability to accelerate sialylglycoconjugate biosynthesis. Hence the cells restoration to a better condition for normal biological function to respond to factors which may affect the respiratory surface thereby leading to respiratory conditions can be achieved providing the sialylglycoconjugate are restored on the surface of the cell.

This method involves obtaining a cell, preferably a respiratory cell, which has reduced sialylglycoconjugates on a surface. This cell is termed as a "naked cell" which is vulnerable to factors which may affect its ability to function normally.

The cell may be derived by subjecting a normal cell such as a respiratory cell to a neuraminidase to remove sialic acid from the sialylglycoconjugates on the surface of the cell. This cell is then measured by the ability of a test compound to restore the sialylglycoconjugates on the surface. The test compound may restore the sialylglycoconjugates by accelerating sialylglycoconjugate biosynthesis or by other means that result in the restoration of the sialylglycoconjugates on the surface of the cell.

The ability to restore the sialylglycoconjugates on the surface of the cells may be measured by the restoration of viability of the cell. The viability of the cell may be measured by any means available to the skilled addressee. However, it may be determined by the cells ability for cellular proliferation. This can be measured by the use of standard cell proliferation kits such as but not limited to Cell Proliferation ELISA kit to measure BrdU incorporated into newly synthesized DNA of replicating cells or by the use of [$^3$H]-thymidine-based cell proliferation assays.

The ability may also be measured by determining the number of sialylglycoconjugates restored on the cell as a consequence of exposure of the cell to the test compound. This can be measured by means available to the skilled addressee such as, but not limited to the use of antibodies to the sialylglycoconjugates.

In yet another embodiment there is provided a method of treating or preventing a respiratory condition in a subject, the method including the step of administering to the subject at least one compound identified by the screening method.

Finally, the invention as hereinbefore described is susceptible to variations, modifications and/or additions other than those specifically described and it is understood that the invention includes all such variations, modifications and/or additions which may be made it is to be understood that various other modifications and/or additions which fall within the scope of the description as hereinbefore described. The following examples are for illustrative purposes only and should not be construed as a limitation of the invention.

EXAMPLES

General Methods Used in the Examples

NMR was recorded on Bruker Avance 300, Xwin-NMR version 3.5 on DPX 300A.

MS was recorded on Mass Spectrometer Waters Micromass ZMD using an ESI (electrospray ionisation probe). The system was run using Water Mass Lynx NT software.

Flash column chromatography was performed on silica gel 60 $F_{245}$ (E. Merck).

Thin Layer Chromatography (TLC) was performed on silica gel precoated plates (E. Merck).

HPLC was run on Waters alliance 2690 separation module, detected by Waters dual wavelength 2487 UV detector, the software was Waters Millenium 32.

Cell culture and cell viability assay

Method 1

Cells used: Small Airway Epithelial Cells (SAEC)

Media: SAGM Bullet kit (SABM+growth supplement)

And/or

Cells used: Normal Human Bronchial Epithelial Cells (NHBE)

Media: BEGM Bullet kit (BEBM+growth supplement)

Experimental details:

Cryopreserved cells ($1\times10^6$ cells in 1 ml) were thawed and cultured on 175 cm$^2$ petri-dish in complete media. The media is removed the next day and replaced with fresh media. The cells are cultured for about 5-6 days to obtain 70-80% confluency. During the growing phase, the media is changed every second day.

When the appropriate confluency is obtained, the media is removed. The monolayer of cells is rinsed with 1×PBS. Following the removal of the PBS, 2 ml of trypsin+EDTA is added. The cells are gently rocked at room temperature for 2 min. The cells are harvested with 1×PBS, centrifuged at 200 g for 10 min. The pellet was resuspended to $5\times10^4$/ml. In a 96-well plate, the cells were aliquoted in 100 μl/well (approx. 5000 cells/well). The cells are incubated at 37° C. for 24 h.

Bacterial neuraminidase (from *Clostridium perfringens*), 10 μl was added to each well to a final concentration of 0.01

U/ml for SAEC and 0.008 u/ml for NHBE. The cells were then incubated for 6 h at 37° C.

Centrifugation of the plate was carried out at 1000 rpm for 10 min, the media aspirated and 200 µl of fresh media added. The plate was centrifuged again, the media replaced with 100 µl of fresh media.

Compounds for test were made up at 6× of the desired concentration; 20 µl of the compound was added to each well in triplicate. The cells were then incubated at 37° C. for 24 h.

The cells were labeled overnight (approx. 16 h) at 37° C. with 10 µl of BrdU label (Cell Proliferation ELISA kit—Roche).

Labeling medium was removed and the cells were fixed and denatured for 30 min at room temperature with Fixing solution supplied by the manufacturer.

Following removal of the fixing solution, 100 µl of anti-BrdU-POD (at the appropriate concentration as suggested by the manufacturer) was added to each well. The plate was incubated at room temperature for 90 min.

The antibody conjugate was removed and the wells washed three times with 200 µl of Washing solution (supplied). After removal or the washing solution, 100 µl of the Substrate solution (supplied) was added; and incubated at room temperature for 30 min. The reaction was stopped with the addition of 50 µl of 1M $H_2SO_4$. Absorbance of the samples was measured at 450 nm (reference wavelength of 690 nm).

Small Airway Epithelial Cells (SAEC) treated with 0.01 U/ml neuraminidase (NA) from *Clostridium perfringens*.

|  | Cell viability (mean ± SEM, n = 20) |
| --- | --- |
| Control (normal cell) | 100% |
| Control treated with NA | 72.82% ± 7.26 |

Normal Human Bronchial Epithelial Cells (NHBE) treated with 0.008 U/ml neuraminidase (NA) from *Clostridium perfringens*.

|  | Cell viability (mean ± SEM, n = 20) |
| --- | --- |
| Control (normal cell) | 100% |
| Control treated with NA | 73.30% ± 7.12 |

The cell viability assay normally gave an operational deviation of ±10%. Therefore, only the results showed the cell viability ≤120% against that of control (treated with neuraminidase) are considered as significant. It is indicated that the compounds with positive results could restore the cell viability within 48 hrs. Among the compounds of Formula (1) and/or (2) the most active compounds with low cytotoxicity were N-acetylmannosamine (Compound 1) and N-acetyl-neuraminic acid (Compound 2).

Method 2
  Cells used: Small Airway Epithelial Cells (SAEC)
  Media: SAGM Bullet kit (SABM+growth supplement)
    And/or
  Cells used: Normal Human Bronchial Epithelial Cells (NHBE)
  Media: BEGM Bullet kit (BEBM+growth supplement)
  Experimental details:

Cryopreserved cells ($1 \times 10^6$ cell in 1 ml) were thawed and cultured on 175 cm² petri-dish in complete media. The media was removed the next day and replaced with fresh media. The cells were cultured for about 5-6 days to obtain 70-80% confluency. During the growing phase, the media was changed every second day.

When the appropriate confluency was obtained, the media was removed. The monolayer of cells was rinsed with 1×PBS. Following the removal of the PBS, 2 ml of trypsin+EDTA was added. The cells were gently rocked at room temperature for 2 min. The cells were harvested with 1×PBS, centrifuged at 200 g for 10 min. The pellet was resuspended to $5 \times 10^4$/ml. In a 96-well plate, the cells were aliquoted in 100 µl/well (approx. 5000 cells/well). The cells were incubated at 37° C. for 24 h.

Viral neuraminidase (from influenza virus NWS/G70C), 10 µl was added to each well to a final concentration of 0.017 µg/ml. The cells were then incubated for 6 h at 37° C.

Centrifugation of the plate was carried out at 1000 rpm for 10 min, the media aspirated and 200 µl of fresh media added. The plate was centrifuged again, the media replaced with 100 µl of fresh media.

Compounds for test were made up at 6× of the desired concentration; 20 µl of the compound is added to each well in triplicate. The cells are then incubated at 37° C. for 24 h.

The cells are labeled overnight (approx. 16 h) at 37° C. with 10 µl of BrdU label (Cell Proliferation ELISA kit—Roche).

Labeling media was removed and the cells are fixed and denatured for 30 min at room temperature with Fixing solution supplied by the manufacturer.

Following removal of the fixing solution 100 µl of anti-BrdU-POD (at the appropriate concentration as suggested by the manufacturer) was added to each well. The plate is incubated at room temperature for 90 min.

The antibody conjugate was removed and the wells washed three times with 200 µl of Washing solution (supplied). After removal of the washing solution, 100 µl of the Substrate solution (supplied) was added and incubated at room temperature for 30 min. The reaction was stopped with the addition of 50 µl of 1M $H_2SO_4$. Absorbance of the samples was measured at 450 nm (reference wavelength of 690 nm).

Example 1

Preparation of N-acetyl-D-mannosamine (1)

[Compound (1), formula (1), B=H, A=NHCOCH$_3$, $R^1$=$R^2$=$R^3$=$R^4$=H]

1 g. of N-acetyl-D-glucosamine obtained by hydrolysis of chitin, was dissolved in 3 ml. of water, then adjusted to pH>11 by using 30% NaOH solution. The mixture was allowed to stand at 20° C.~40° C. for 48 hrs. The resulting solution was neutralized to pH 6.5~7.0 with 5N $H_2SO_4$, then evaporated under reduced pressure to dryness. The solid was refluxed in ethanol for 10 min., cooled to room temperature, and filtered. The filtrate was vacuum evaporated to dryness to afford a white solid which contains 85% N-acetyl-D-mannosamine and 15% N-acetyl-D-glucosamine, determined by $^1$H-nmr. This solid was fractionally recrystallized from ethanol/isopropanol/EA to afford the title compound as a white solid (125 mg, 62.5% based on 20% conversion rate of N-acetyl-D-mannosamine). The unreacted N-acetyl-D-glucosamine (0.8 g) could be reused for next batch of reaction.

$^1$H-nmr (D$_2$O) δ (ppm)

5.15 (d, 0.7H), 3.85~3.32 (m, 6.3H), 1.99 (s, 3H).

MS 222 (M+1)

Example 2

Preparation of N-acetyl-neuraminic acid Sodium Salt (2)

[Compound (2), Formula (2), $R^8=R^{10}=R^{11}=R^{12}=R^{13}=H$, $R^9=Na$]

To a pH 7.0~7.5 solution of N-acetylmannosamine (2.7 g, 12.2 mmole) and sodium pyruvate (2.7 g, 24.5 mmole) in water (15 ml) was added a dialysis bag (cut off MW of 20,000) containing N-acetylneuraminate lyase [EC 4.1.3.3] (25 units) in a reaction mixture of N-acetylmannosamine (0.54 g) and sodium pyruvate (0.54 g) in water (3 ml) at pH 7.0-7.5. The reaction mixture was shaken at 60 r.p.m. at 30° C. for 5 days. The enzyme bag was removed and reused for new batch of reaction. The reaction mixture was diluted with water (15 ml), then passed through a column of Amberlite IRA-400 (HCOO⁻ form) (150 ml). The resin was then washed with water (300 ml), eluted with 0.5M HCOOH solution. The eluate was collected and vacuum evaporated to dryness. The residue was dissolved in water (2 ml) then diluted with glacial acetic acid (10 ml) at 4° C. overnight, filtered the crystals, washed with EtOH, dried to afford N-acetylneuraminic acid as white crystalline powder (1.5 g, 39.8%).

$^1$H-nmr (D$_2$O) δ (ppm)
4.00 (m, 1H), 3.97 (m, 1H), 3.87 (d, 1H), 3.77 (dd, 1H), 3.67 (m, 1H), 3.55 (dd, 1H), 3.48 (d, 1H), 2.24 (dd, 1H, J=13.2 H$_z$, 5.1H$_z$), 1.98 (s, 3H), 1.83 (dd, 1H, J=13.2 H$_z$, 11.5 H$_z$).
MS 310 (M+1)

N-acetylneuraminic acid (1 g, 3.23 mmol) was dissolved in water (20 ml), then stirred with NaHCO$_3$ (0.26 g, 3.09 mmol to $_p$H 6~6.5), after freeze-dried to afford the title product as white powder (1.05 g, 98%).

Example 3

Preparation of ethyl N-acetyl-neuraminate (3)

To a suspension of N-acetyl-neuraminic acid (1 g, 3.23 mmole) in anhydrous ethanol (75 ml) was added 1.5 ml acetyl chloride. The mixture was sealed and stirred at room temperature for 16 hrs. to form a clear solution. The resulting solution was vacuum evaporated to dryness. The white solid was washed with ethyl acetate and vacuum dried to afford the title compound as a white solid (1 g, 91.7%).

$^1$H-nmr (D$_2$O) δ ppm)
4.27 (q, 2H), 4.04 (m, 2H), 3.91 (d, 1H), 3.78 (dd, 1H), 3.68 (dd, 1H), 3.57 (dd, 1H), 3.52 (d, 1H), 2.28 (dd, 1H), 2.01 (s, 3H), 1.88 (dd, 1H), 1.28 (t, 3H).
MS 338 (M+1), 360 (M+23)

Example 4

Preparation of ethyl 5-acetamido-4,7,8,9,-tetra-o-acetyl-3,5-dideoxy-β-D-glycero-D-galacto-2-nonulopyranosonate (ethyl 5-acetamido-4,7,8,9-tetra-o-acetyl-neuraminate) (4)

To an agitated solution of acetic anhydrade (0.72 g) and aqueous 60% perchloric acid (5 μl) at 40° C. was added in portion over 30 mins ethyl 5-acetamido-neuraminate (230 mg, 0.68 mmol). The resulting mixture was stirred at 40° C. for 2 hrs. Then it was cooled to room temperature, diluted with cold water (10 ml), saturated with ammonium sulfate, extracted with ethyl acetate (40 ml×3). The organic extracts were combined and washed with saturated NaHCO$_3$ solution and water successively. The organic layer was dried over MgSO$_4$, and evaporated in vacuo to dryness. The residue was dissolved in ethyl acetate, diluted with hexane to give the title compound as a white crystal (223 mg, 65%).

$^1$H-nmr (CDCl$_3$) δ(ppm)
5.71 (m, 1H), 5.36 (dd, 1H, J=1.5H$_z$, 5.6H$_z$), 5.25 (ddd, 1H, J=2.4H$_z$, 7.5H$_z$), 5.22 (ddd, 1H, J=11.4H$_z$, 5.4H$_z$, 9.5H$_z$), 4.51 (dd, 1H, J=12.4H$_z$), 4.47 (d, 1H, J=0.8H$_z$), 4.21~4.13 (m, 4H), 4.03 (dd, 1H), 2.26 (ddd, 1H, 12.8H$_z$), 2.19 (dd, 1H), 2.15, 2.11, 2.03, 2.02, and 1.91 (5s, 15H), 1.29 (t, 3H, J=7.2H$_z$).
MS 506 (M+1)

Example 5

Preparation of cytidine-5'-monophospho-5-acetamido-3,5,-dideoxy-β-D-glycero-D-galacto-2-nonulopyranosonic acid (CMP-sialic acid) (5)

N-acetylneuraminic acid (100 mg, 0.32 mmole), and cytidine-5'-triphosphate sodium salt (156.3 mg, 0.32 mmole) were dissolved in 32 ml of Tris-HCl buffer (100 mM, pH 8.8) containing MgCl$_2$ (20 mM). To this solution was added CMP-Neu5Ac synthetase (5 mg, from *N. meningitidis*). The reaction mixture was incubated at 37° C. for 2~3 hrs. while monitored by TLC (silica gel, EtOH:1M NH$_4$HCO$_3$=7:3). The reaction mixture was diluted with methanol (50 ml) and filtered off. The filtrate was evaporated under reduced pressure to dryness. The residue was chromatographed on Bio Gel P-2 resin (50 ml) to afford the title compound after freeze-dried as a white crystalline powder (147 mg, 75%).

HPLC analysis:
C-18 column.
Mobile phase: buffer A (0.1 M potassium phosphate buffer. Supplemented with 8 mM tetra-butylammonium hydrogensulfate, pH 5.3) and buffer B (70% buffer A plus 30% methanol, pH 5.9)
Gradient condition:
100% buffer A for 2.5 min, 0~40% buffer B for 7.5 min, 40~100% buffer B for 1 min, 100% buffer B for 4 min, 100~0% buffer B for 1 min, followed by an equilibration phase of 100% buffer A for 4 min.
Flow rate: 1 ml/min.
U.V. detection at 270 nm $^1$H-nmr (D$_2$O) δ(ppm)
7.87 (d, 1H, J=7.6 H$_z$), 6.25 (d, 1H, J=7.6 H$_z$), 5.91 (d, 1H, J=4.4H$_z$), 4.26~4.20 (m, 2H), 4.17~4.10 (m, 3H), 4.09~3.98 (m, 2H), 3.90~3.80 (m, 3H), 3.59~3.40 (m, 2H), 2.42 (dd, 1H, J=4.8, 13.2 H$_z$), 1.98 (s, 3H), 1.60 (dt, 1H, J=5.6, 12.6 H$_z$).
MS 635 (M$^{2-}$+Na$^+$)

Example 6

Preparation of ethyl 5-acetamido-8,9-O-isopropylidine-neuraminate (6)

To a solution of ethyl 5-acetamido-neuraminate (150 mg, 0.445 mmole) in anhydrous DMF (2 ml) was added 2,2-dimethoxypropane (1 ml, 8 mmole) and Amberlyst 15 (50 mg). The mixture was stirred at 60° C. for 7 hrs, then cooled to room temperature and filtered. The filtrate was evaporated under reduced pressure to dryness. TLC (silica gel, EA/MeOH=10:4) indicated the completion of the reaction. The residue was redissolved in EA/MeOH=10/1 (1 ml), then flash column chromatographed. The required fractions were combined and evaporated in vacuo to dryness to afford the title compound as a white form (135 mg, 75%).

$^1$H-nmr (D$_2$O) δ(ppm)

4.28~4.23 (m, 2H), 4.23~4.11 (m, 2H), 4.08~3.92 (m, 2H), 3.96~3.52 (m, 3H), 2.31 (dd, 1/3H), 2.23 (dd, 2/3H), 1.99 (s, 3H), 1.82 (dd, 2/3H), 1.70 (dd, 1/3H), 1.36 (s, 3H), 1.32 (s, 3H), 1.25 (t, 3H).

MS 428 (M+Na)

Example 7

Activity of Compound (1) on Recovery of the Viability of Small Airways Epithelial Cells (SAEC)

Compound (1) [Formula (1), B=H, A=NHCOCH$_3$, R$^1$=R$^2$=R$^3$=R$^4$=H]

|  | Cell viability (mean ± SEM, n = 3) |
| --- | --- |
| Control (treated with neuraminidase) | 100% |
| Compound (1) 50 µg/ml | 171% ± 6.33 |
| 12.5 µg/ml | 175% ± 2.33 |
| 3.1 µg/ml | 146% ± 7.10 |
| 0.77 µg/ml | 139% ± 3.46 |
| 0.19 µg/ml | 157% ± 4.47 |

Example 8

Activity of Compound (1) on Recovery of the Viability of Normal Human Bronchial/Tracheal Epithelial Cells (NHBE)

|  | Cell viability (mean ± SEM, n = 3) |
| --- | --- |
| Control (treated with neuraminidase) | 100% |
| Compound (1) 50 µg/ml | 125% ± 3.20 |
| 12.5 µg/ml | 124% ± 2.21 |
| 3.1 µg/ml | 120% ± 0.79 |
| 0.77 µg/ml | 119% ± 2.23 |
| 0.19 µg/ml | 116% ± 1.42 |

Example 9

Activity of Compound (2) on Recovery of the Viability of SAEC

Compound (2) [Formula (2), R$^8$=R$^{10}$=R$^{11}$=R$^{12}$=R$^{13}$=H, R$^9$=Na]

|  | Cell viability (mean ± SEM, n = 3) |
| --- | --- |
| Control (treated with neuraminidase) | 100% |
| Compound (2) 50 µg/ml | 129% ± 3.96 |
| 12.5 µg/ml | 127% ± 2.51 |
| 3.1 µg/ml | 115% ± 1.56 |
| 0.77 µg/ml | 130% ± 2.18 |
| 0.19 µg/ml | 129% ± 3.22 |
| 0.05 µg/ml | 138% ± 0.50 |
| 0.012 µg/ml | 140% ± 2.15 |
| 0.003 µg/ml | 124% ± 1.91 |

Example 10

Activity of Compound (2) on Recovery of the Viability of the NHBE

|  | Cell viability (mean ± SEM, n = 3) |
| --- | --- |
| Control (treated with neuraminidase) | 100% |
| Compound (2) 50 µg/ml | 137% ± 1.00 |
| 12.5 µg/ml | 127% ± 4.02 |
| 3.1 µg/ml | 117% ± 3.22 |
| 0.77 µg/ml | 117% ± 0.68 |
| 0.19 µg/ml | 126% ± 0.21 |

Example 11

Activity of Compound (3) on Recovery of the Viability of SAEC

Compound (3) [Formula (2), R$^8$=R$^{10}$=R$^{11}$=R$^{12}$=R$^{13}$=H, R$^9$=C$_2$H$_5$]

|  | Cell viability (mean ± SEM, n = 3) |
| --- | --- |
| Control (treated with neuraminidase) | 100% |
| Compound (3) 50 µg/ml | 104% ± 1.66 |
| 12.5 µg/ml | 107% ± 0.41 |
| 3.1 µg/ml | 109% ± 1.41 |
| 0.77 µg/ml | 103% ± 3.43 |
| 0.05 µg/ml | 104% ± 1.46 |

Example 12

Activity of Compound (3) on Recovery of the Viability of NHBE

|  | Cell viability (mean ± SEM, n = 3) |
| --- | --- |
| Control (treated with neuraminidase) | 100% |
| Compound (3) 50 µg/ml | 106% ± 1.35 |
| 12.5 µg/ml | 100% ± 0.88 |
| 3.1 µg/ml | 113% ± 0.84 |
| 0.77 µg/ml | 111% ± 4.73 |
| 0.19 µg/ml | 114% ± 5.14 |
| 0.05 µg/ml | 130% ± 5.19 |
| 0.012 µg/ml | 130% ± 6.11 |
| 0.003 µg/ml | 154% ± 4.91 |

Example 13

Activity of Compound (4) on Recovery of the Viability of SAEC

Compound (4) [Formula (2), R$^8$=H, R$^9$=C$_2$H$_5$, R$^{10}$=R$^{11}$=R$^{12}$=R$^{13}$=CH$_3$CO]

|  | Cell viability (mean ± SEM, n = 3) |
| --- | --- |
| Control (treated with neuraminidase) | 100% |
| Compound (4) 50 µg/ml | 99% ± 4.00 |
| 12.5 µg/ml | 97% ± 3.00 |
| 3.1 µg/ml | 100% ± 1.80 |
| 0.77 µg/ml | 115% ± 4.40 |
| 0.19 µg/ml | 121% ± 1.80 |
| 0.05 µg/ml | 106% ± 6.09 |
| 0.012 µg/ml | 116% ± 0.10 |
| 0.003 µg/ml | 110% ± 1.09 |

Example 14

Activity of Compound (4) on Recovery of Viability of NHBE

|  | Cell viability (mean ± SEM, n = 3) |
| --- | --- |
| Control (treated with neuraminidase) | 100% |
| Compound (4) 50 µg/ml | 110% ± 1.02 |
| 12.5 µg/ml | 117% ± 0.29 |
| 3.1 µg/ml | 111% ± 4.54 |
| 0.77 µg/ml | 110% ± 3..77 |
| 0.19 µg/ml | 125% ± 1.46 |
| 0.05 µg/ml | 115% ± 5.22 |
| 0.012 µg/ml | 113% ± 6.85 |
| 0.003 µg/ml | 83% ± 0.88 |

Example 15

Activity of Compound (5) on Recovery of the Viability of SAEC

Compound (5) [formula (2), $R^8$=cytidine monophosphate, $R^9$=$R^{10}$=$R^{11}$=$R^{12}$=$R^{13}$=H]

|  | Cell viability (mean ± SEM, n = 3) |
| --- | --- |
| Control (treated with neuraminidase) | 100% |
| Compound (5) 50 µg/ml | 116% ± 5.30 |
| 12.5 µg/ml | 108% ± 1.20 |
| 3.1 µg/ml | 141% ± 1.70 |
| 0.77 µg/ml | 141% ± 1.09 |
| 0.19 µg/ml | 145% ± 4.89 |

Example 16

Activity of Compound (5) on Recovery of the Viability of NHBE

|  | Cell viability (mean ± SEM, n = 3) |
| --- | --- |
| Control (treated with neuraminidase) | 100% |
| Compound (5) 50 µg/ml | 116% ± 0.93 |
| 12.5 µg/ml | 109% ± 3.60 |
| 3.1 µg/ml | 112% ± 2.59 |
| 0.77 µg/ml | 109% ± 1.92 |
| 0.19 µg/ml | 89% ± 0.79 |

Example 17

Activity of Compound (6) on Recovery of the Viability of SAEC

Compound (6) [formula (2), $R^8$=H, $R^9$=$C_2H_5$, $R^{10}$=$R^{11}$=H, $R^{12}$ and $R^{13}$=>C($CH_3$)$_2$]

|  | Cell viability (mean ± SEM, n = 3) |
| --- | --- |
| Control (treated with neuraminidase) | 100% |
| Compound (6) 50 µg/ml | 119% ± 3.17 |
| 12.5 µg/ml | 125% ± 1.13 |
| 3.1 µg/ml | 123% ± 5.02 |
| 0.77 µg/ml | 135% ± 3.27 |
| 0.19 µg/ml | 140% ± 1.92 |

Example 18

Activity of Compound (6) on Recovery of the Viability of NHBE

|  | Cell viability (mean ± SEM, n = 3) |
| --- | --- |
| Control (treated with neuraminidase) | 100% |
| Compound (6) 50 µg/ml | 90% ± 8.36 |
| 12.5 µg/ml | 99% ± 3.17 |
| 3.1 µg/ml | 121% ± 2.10 |
| 0.77 µg/ml | 128% ± 3.60 |
| 0.19 µg/ml | 133% ± 0.88 |
| 0.05 µg/ml | 127% ± 1.81 |
| 0.012 µg/ml | 122% ± 3.33 |
| 0.003 µg/ml | 141% ± 4.70 |

Example 19

Activity of Compound (7) on Recovery of the Viability of SAEC

Compound (7) [Formula (1), B=H, A=$NHCOCH_3$, $R^1$=$R^2$=$R^3$=$R^4$=$COCH_3$]

|  | Cell viability (mean ± SEM, n = 3) |
| --- | --- |
| Control (treated with neuraminidase) | 100% |
| Compound (7) 50 µg/ml | 73% ± 2.18 |
| 12.5 µg/ml | 134% ± 0.81 |
| 3.1 µg/ml | 103% ± 1.14 |
| 0.77 µg/ml | 112% ± 1.29 |
| 0.19 µg/ml | 105% ± 2.01 |
| 0.05 µg/ml | 128% ± 1.98 |
| 0.012 µg/ml | 105% ± 1.83 |
| 0.003 µg/ml | 102% ± 0.62 |

Example 20

Activity of Compound (7) on Recovery of the Viability of NHBE

|  | Cell viability (mean ± SEM, n = 3) |
|---|---|
| Control (treated with neuraminidase) | 100% |
| Compound (7) 50 µg/ml | 54% ± 0.98 |
| 12.5 µg/ml | 117% ± 4.12 |
| 3.1 µg/ml | 98% ± 5.65 |
| 0.77 µg/ml | 99% ± 1.93 |
| 0.19 µg/ml | 100% ± 0.66 |
| 0.05 µg/ml | 104% ± 5.85 |
| 0.012 µg/ml | 103% ± 4.70 |
| 0.003 µg/ml | 85% ± 2.71 |

Example 21

Activity of Compound (8) on Recovery of the Viability of SAEC

Compound (8) [Formula (1), B=H, A=NHCOCH$_3$, R$^1$=H, R$^2$=R$^3$=R$^4$=COCH$_3$]

|  | Cell viability (mean ± SEM, n = 3) |
|---|---|
| Control (treated with neuraminidase) | 100% |
| Compound (8) 50 µg/ml | 91% ± 3.36 |
| 12.5 µg/ml | 104% ± 1.95 |
| 3.1 µg/ml | 109% ± 2.79 |
| 0.77 µg/ml | 103% ± 3.21 |
| 0.19 µg/ml | 115% ± 3.52 |
| 0.05 µg/ml | 109% ± 1.16 |
| 0.012 µg/ml | Not determined |
| 0.003 µg/ml | 125% ± 8.51 |

Example 22

Activity of Compound (8) on Recovery of the Viability of NHBE

|  | Cell viability (mean ± SEM, n = 3) |
|---|---|
| Control (treated with neuraminidase) | 100% |
| Compound (8) 50 µg/ml | 42% ± 1.55 |
| 12.5 µg/ml | 81% ± 0.60 |
| 3.1 µg/ml | 111% ± 2.44 |
| 0.77 µg/ml | 133% ± 2.09 |
| 0.19 µg/ml | 96% ± 1.21 |
| 0.05 µg/ml | 93% ± 1.38 |
| 0.012 µg/ml | 118% ± 3.19 |
| 0.003 µg/ml | 129% ± 1.70 |

Example 23

Activity of Compound (9) on Recovery of the Viability of SAEC

Compound (9) [Formula (1), A=H, B=NHCOCH$_3$, R$^1$=R$^2$=R$^3$=R$^4$=H]

|  | Cell viability (mean ± SEM, n = 3) |
|---|---|
| Control (treated with neuraminidase) | 100% |
| Compound (9) 50 µg/ml | 122% ± 3.21 |
| 12.5 µg/ml | 119% ± 3.04 |
| 3.1 µg/ml | 115% ± 3.17 |
| 0.77 µg/ml | 120% ± 3.14 |
| 0.19 µg/ml | 121% ± 2.42 |

Example 24

Activity of Compound (9) on Recovery of the Viability of NHBE

|  | Cell viability (mean ± SEM, n = 3) |
|---|---|
| Control (treated with neuraminidase) | 100% |
| Compound (9) 50 µg/ml | 106% ± 2.52 |
| 12.5 µg/ml | 106% ± 3.49 |
| 3.1 µg/ml | 108% ± 3.24 |
| 0.77 µg/ml | 107% ± 1.26 |
| 0.19 µg/ml | 107% ± 3.41 |

Example 25

Activity of D-Glucose on Recovery of the Viability of SAEC

|  | Cell viability (mean ± SEM, n = 3) |
|---|---|
| Control (treated with neuraminidase) | 100% |
| D-Glucose 50 µg/ml | 94% ± 3.04 |
| 12.5 µg/ml | 103% ± 1.05 |
| 3.1 µg/ml | 101% ± 2.30 |

Example 26

Activity of D-Glucose on Recovery of the Viability of NHBE

|  | Cell viability (mean ± SEM, n = 3) |
|---|---|
| Control (treated with neuraminidase) | 100% |
| D-Glucose 50 µg/ml | 106% ± 2.76 |
| 12.5 µg/ml | 104% ± 2.13 |
| 3.1 µg/ml | 107% ± 3.05 |
| 0.77 µg/ml | 99% ± 3.15 |
| 0.19 µg/ml | 104% ± 2.96 |

Example 27

Activity of Compound (1) at High Concentration on Recovery of the Viability of SAEC

|  | Cell viability (mean ± SEM, n = 3) |
|---|---|
| Control (treated with neuraminidase) | 100% |
| Compound (1) 5 mg/ml | 118% ± 2.15 |
| 1.25 mg/ml | 121% ± 3.02 |
| 312.5 µg/ml | 115% ± 1.51 |
| 78.1 µg/ml | 127% ± 2.30 |

Example 28

Activity of Compound (1) at High Concentration on Recovery of the Viability of NHBE

|  | Cell viability (mean ± SEM, n = 3) |
|---|---|
| Control (treated with neuraminidase) | 100% |
| Compound (1) 5 mg/ml | 116% ± 2.11 |
| 1.25 mg/ml | 125% ± 2.02 |
| 312.5 µg/ml | 131% ± 3.04 |
| 78.1 µg/ml | 128% ± 1.85 |

Example 29

Activity of Compound (2) at High Concentration on Recovery of the Viability of SAEC

|  | Cell viability (mean ± SEM, n = 3) |
|---|---|
| Control (treated with neuraminidase) | 100% |
| Compound (2) 5 mg/ml | 129% ± 1.76 |
| 1.25 mg/ml | 115% ± 1.38 |
| 312 µg/ml | 118% ± 1.95 |
| 78.1 µg/ml | 135% ± 2.06 |

Example 30

Activity of Compound (2) at High Concentration on Recovery of the Viability of NHBE

|  | Cell viability (mean ± SEM, n = 3) |
|---|---|
| Control (treated with neuraminidase) | 100% |
| Compound (2) 5 mg/ml | 122% ± 2.05 |
| 1.25 mg/ml | 129% ± 3.13 |
| 312.5 µg/ml | 118% ± 2.17 |
| 78.1 µg/ml | 107% ± 1.38 |

Example 31

Activity of Compound (9) at High Concentration on Recovery of the Viability of SAEC

|  | Cell viability (mean ± SEM, n = 3) |
|---|---|
| Control (treatment with neuraminidase) | 100% |
| Compound (9) 5 mg/ml | 83% ± 2.85 |
| 1.25 mg/ml | 96% ± 3.16 |
| 312.5 µg/ml | 90% ± 3.28 |
| 78.1 µg/ml | 100% ± 2.92 |

Example 32

Activity of Compound (9) at High Concentration on Recovery of the Viability of NHBE

|  | Cell viability (mean ± SEM, n = 3) |
|---|---|
| Control (treated with neuraminidase) | 100% |
| Compound (9) 5 mg/ml | 76% ± 2.71 |
| 1.25 mg/ml | 96% ± 2.42 |
| 312.5 µg/ml | 95% ± 2.85 |
| 78.1 µg/ml | 125% ± 3.23 |

Example 33

Activity of a Mixture of Compound (1) (85%) and Compound (9) (15%) at High Concentration on Recovery of the Viability of SAEC

|  | Cell viability (mean ± SEM, n = 3) |
|---|---|
| Control (treated with neuraminidase) | 100% |
| Mixture of compound (1) and (9) 5 mg/ml | 88% ± 1.82 |
| 1.25 mg/ml | 91% ± 2.03 |
| 312.5 µg/ml | 87% ± 2.52 |
| 78.1 µg/ml | 94% ± 1.91 |

Example 34

Activity of a Mixture of Compound (1) (85%) and Compound (9) (15%) at High Concentration on Recovery of the Viability of NHBE

|  | Cell viability (mean ± SEM, n = 3) |
|---|---|
| Control (treated with neuraminidase) | 100% |
| Mixture of compound (1) and (9) 5 mg/ml | 89% ± 2.31 |
| 1.25 mg/ml | 107% ± 2.48 |
| 312.5 µg/ml | 105% ± 2.02 |
| 78.1 µg/ml | 95% ± 3.12 |

Example 35

Activity of a Mixture of Compound (1) (85%) and Compound (9) (15%) on Recovery of the Viability of SAEC

|  | Cell viability (mean ± SEM, n = 3) |
| --- | --- |
| Control (treated with neuraminidase) | 100% |
| Mixture of compound (1) and (9 50 μg/ml | 101% ± 3.41 |
| 12.5 μg/ml | 107% ± 3.91 |
| 3.1 μg/ml | 121% ± 4.82 |
| 0.77 μg/ml | 120% ± 4.11 |
| 0.19 μg/ml | 115% ± 4.02 |
| 0.05 μg/ml | 113% ± 4.30 |
| 0.01 μg/ml | 107% ± 4.12 |
| 0.003 μg/ml | 108% ± 4.20 |

Example 36

Activity of a Mixture of Compound (1) (85%) and Compound (9) (15%) on Recovery of the Viability of NHBE

|  | Cell viability (mean ± SEM, n = 3) |
| --- | --- |
| Control (treated with neuraminidase) | 100% |
| Mixture of compound (1) and (9) 50 μg/ml | 121% ± 2.05 |
| 12.5 μg/ml | 109% ± 1.98 |
| 3.1 μg/ml | 115% ± 1.76 |

Example 37

Cough Experiments on Guinea Pigs[9][10]

Male guinea pigs were housed in pens and have access to water and food ad libitum. This study was approved by Bio21 Institute Animal Ethics Committee.

Twenty four Conscious male Hartley guineapigs (500~550 g) were divided into A, B, C three groups (8 animals for each group), and pretreated with either 5 units/ml solution of neuraminidase (Sigma N2133, lyophilized powder, Type X, 150~400 units/mg protein) in water (group B and C) or saline alone (Group A) via an aerosol for 5 minutes on day one. Then, on day one, two and three, the guineapigs were either orally administered with 500 mg/kg of compound (1) (Group C), or water alone (Group A and B). On day four, all the animals were challenged with 0.5M citric acid solution (nebulised, 10 minutes exposure). The cough frequency, times to the 1st, 2nd and third cough, and times to the 1st nose rubs were then recorded over a period of 15 minutes. The results indicated a trend that compound (1) helped to restore the damages caused by neuraminidase.

|  | Cough frequency (in 15 minutes) |
| --- | --- |
| Group A (Saline only, as control) | 13 ± 2.5 |
| Group B (treated with neuraminidase, as negative control) | 19 ± 2.5 |
| Group C (firstly treated with neuraminidase, then with compound (1) for 3 days) | 16 ± 2.2 |

|  | Time (seconds) to the | | |
| --- | --- | --- | --- |
|  | 1st cough | 2nd cough | 3rd cough |
| Group A (water only, as control) | 87 ± 10 | 157 ± 23 | 200 ± 25 |
| Group B (treated with neuraminidase, as negative control) | 70 ± 11 | 109 ± 6 | 150 ± 20 |
| Group C (firstly treated with neuraminidase, Then treated with compound (1) for 3 days) | 85 ± 15 | 137 ± 31 | 220 ± 10 |

|  | Time (second) to the 1st nose rubs |
| --- | --- |
| Group A (water only, as control) | 50 ± 4.3 |
| Group B (treated with neuraminidase, as negative control) | 27.7 ± 3.6 |
| Group C (firstly treated with neuraminidase, then treated with compound (1) for 3 days) | 49 ± 6.5 |

Using compound (2) instead of compound (1) by the same experimental protocol, the similar results were obtained.

REFERENCES

[1] Edelman, G. M. and Crossin, K. L. Cell adhesion molecules: Implications for a molecular histology. Annu. Rev. Biochem. 60, 155~190 (1991).

[2] Varki A. Divesity in the sialic acids. Glycobiology 2, 25~40 (1992).

[3] Schauer, R., et al. Biochemistry and role of sialic acids. In: Biology of the sialic acids. A. Rosenberg, ed. New York, USA. pp 7~67 (1995).

[4] Rens-Domiano, S. and Reisine, T. Structural analysis and functional role of the carbohydrate component of somatostatin receptors. J. Biol. Chem. 266, 20094~20102 (1991).

[5] Keppler, O. T., et al. Science 284(5418), 1372~1376 (1999).

[6] Miyata, T., et al. Archives internationales de pharmacodynamie et de therapie, 296, 202~9 (1988).

[7] Miyata, T., et al. Archives internationales de pharmacodynamie et de therapie, 304, 277~89 (1990).

[8] Amir, S. M., et al. Nature, 211(5052), 976~7(1966).

[8b] B. Galeano et al. Mutation in the key enzyme of sialic acid biosynthesis causes severe glomerular proteinuria and is rescued by N-acetylmannosamine. J. Clin. Invest. 2007 117 (6) 1585~1594.

[8c] U.S. Provisional Application No. 60/932,451 filed 31 May 2007.

[9] Laude, E. A. et al, "A comparative study of the effects of Citric acid, Capsaicin and Resiniferatoxin on the Cough challenge in Guinea-pig and Man". Pulmonary Pharmacology 6, 171~175 (1993).

[10] Tanaka, M. et al, "Mechanisms of Capsaicin- and Citric-acid-induced Cough Reflexes in Guinea pig". J. Pharmacol. Sci., 99, 77~82 (2005).

Future patent applications may be filed on the basis of or claiming priority from the present application. It is to be understood that the following claims are provided by way of example only, and are not intended to limit the scope of what may be claimed in any such future application. Features may be added to or omitted from the claims at a later date so as to further define or re-define the invention or inventions.

Finally, it is to be understood that various other modifications and/or alterations may be made without departing from the spirit of the present invention as outlined herein.

The invention claimed is:

1. A method of promoting recovery of cell viability of a damaged respiratory cell in a subject post a viral or bacterial respiratory infection, the method including a step of administering to the subject post a viral or bacterial respiratory infection an effective amount of at least one pharmaceutically acceptable compound that accelerates sialylglycoconjugate biosynthesis to restore sialylglycoconjugates on a surface of the respiratory cell and wherein the at least one pharmaceutically acceptable compound is selected from the group consisting of compounds of Formula (1) and compounds of Formula (2) wherein Formula (1) has the formula:

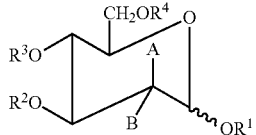

Formula (1)

wherein, $R^1$, $R^2$, $R^3$, are the same or different and are each independently selected from the group consisting of H, $CH_3$, $(CH_2)_nCH_3$ (n=1-20), $CH_2Ph$, $COCR^5R^6R^7$, and CO-active esters;

$R^5$, $R^6$, $R^7$ are the same or different and are each independently selected from the group consisting of H, $CH_3$, $(CH_2)_nCH_3$ (n=1-20), $C_6H_5$, $CH_2Ph$, and $CH_3CH_2(OCH_2CH_2)_mCH_3$ (m=1-200);

$R^4$ is the same or different to $R^1$, $R^2$, $R^3$ and is selected from the group consisting of H, $CH_3$, $(CH_2)_nCH_3$ (n=1-20), $CH_2Ph$, $COCR^5R^6R^7$, CO-active esters and

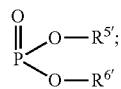

$R^{5'}$, $R^{6'}$ are the same or different and are each independently selected from the group consisting of H or a pharmaceutically suitable inorganic or organic salt, and a pharmaceutically suitable ester;

one of A and B is H, with the proviso that:

when B is H, then A is selected from the group consisting of $NHCOCH_3$, $NH_2$, OH, and $NH_2.HX$ or when A is H, B is selected from the group consisting of $NH_2$ and $NH_2.HX$, wherein HX represents a pharmaceutically suitable inorganic or organic acid; and wherein Formula (2) has the formula

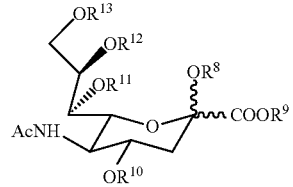

Formula (2)

wherein, $R^8$ is selected from the group consisting of H, $CH_3$, $(CH_2)_nCH_3$ (n=1-20), $CH_2Ph$, $COCH_2Ph$, CO-active ester and $COCR^{14}R^{15}R^{16}$; wherein $R^{14}$, $R^{15}$, $R^{16}$ are the same or different and are each independently selected from the group consisting of H, $CH_3$, $(CH_2)_nCH_3$ (n=1-20), $C_6H_5$, $CH_2Ph$, $CH_2CH_2(OCH_2CH_2)_mCH_3$ (m=1-200), cytidine, cytidine monophosphate, cytidine diphosphate, cytidine triphosphate, adenosine, adenosine monophosphate, adenosine diphosphate, and adenosine triphosphate;

$R^9$ is selected from the group consisting of H, $CH_3$, a pharmaceutically acceptable inorganic or organic salt, a pharmaceutically suitable active ester, and $CH_2CR^{17}R^{18}R^{19}$, wherein $R^{17}$, $R^{18}$, $R^{19}$ are the same or different and are each independently selected from the group consisting of H, $CH_3$, $(CH_2)_nCH_3$ (n=1-20), $CH_2CH_2(OCH_2CH_2)_mCH_3$ (m=1-200), $C_6H_5$, and $CH_2Ph$;

$R^{10}$, $R^{11}$, $R^{12}$ are the same or different and are each independently selected from the group consisting of H, $CH_3$, $(CH_2)_nCH_3$ (n=1-20), $CH_2Ph$, active ester, and $COCR^{20}R^{21}R^{22}$, wherein $R^{20}$, $R^{21}$, and $R^{22}$ are the same or different and are each independently selected from the group consisting of H, $CH_3$, $(CH_2)_nCH_3$ (n=1-20), $C_6H_5$, $CH_2Ph$, and $CH_2CH_2(OCH_2CH_2)_mCH_3$ (m=1-200);

$R^{13}$ is the same or different from $R^{10}$, $R^{11}$, $R^{12}$ and is selected from the group consisting of H, $CH_3$, $(CH_2)_nCH_3$ (n=1-20), $CH_2Ph$, active ester, and $COCR^{20}R^{21}R^{22}$, wherein $R^{20}$, $R^{21}$, and $R^{22}$ are the same or different and are each independently selected from the group consisting of H, $CH_3$, $(CH_2)_nCH_3$ (n=1-20), $C_6H_5$, $CH_2Ph$, $CH_2CH_2(OCH_2CH_2)_mCH_3$ (m=1-200) and

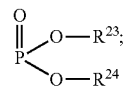

$R^{23}$, $R^{24}$ are the same or different and are each independently selected from the group consisting of H, $CH_3$, $(CH_2)_nCH_3$ (n=1-20), $CH_2CH_2(OCH_2CH_2)_mCH_3$ (m=1-200), $CH_2Ph$, or active ester, and $CH_2CR^{25}R^{26}R^{27}$, or pharmaceutically acceptable inorganic or organic salt, and $R^{25}$, $R^{26}$, $R^{27}$ are the same or different and are each independently selected from the group consisting of H, $CH_3$, $(CH_2)_nCH_3$ (n=1-20), $C_6H_5$, and $CH_2Ph$.

2. The method according to claim 1, wherein the at least one pharmaceutically acceptable compound is selected from the group consisting of N-acetylmannosamine, N-acetylneuraminic acid, CMP-sialic acid, a pharmaceutically acceptable salt thereof, and a combination thereof.

3. A method of treating a respiratory condition resulting from a damaged respiratory cell in a subject post a viral or bacterial respiratory infection, the method including a step of administering to the subject post a viral or bacterial respiratory infection an effective amount of at least one pharmaceutically acceptable compound that accelerates sialylglycoconjugate biosynthesis to restore sialylglycoconjugates on the surface of a respiratory cell in the subject to promote recovery of cell viability of a damaged respiratory cell, wherein the subject suffers from a respiratory condition selected from the group consisting of cough, acute bronchitis, chronic bronchitis, chronic obstructive pulmonary disease, and cystic fibrosis and wherein the at least one pharmaceutically acceptable compound is selected from the group consisting of compounds of Formula (1) and compounds of Formula (2) wherein Formula (1) has the formula:

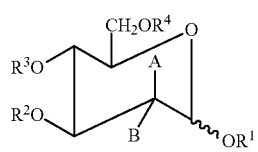

Formula (1)

wherein, $R^1$, $R^2$, $R^3$, are the same or different and are each independently selected from the group consisting of H, $CH_3$, $(CH_2)_nCH_3$ (n=1-20), $CH_2Ph$, $COCR^5R^6R^7$, and CO-active esters;

$R^5$, $R^6$, $R^7$ are the same or different and are each independently selected from the group consisting of H, $CH_3$, $(CH_2)_nCH_3$ (n=1-20), $C_6H_5$, $CH_2Ph$, and $CH_3CH_2(OCH_2CH_2)_mCH_3$ (m=1-200);

$R^4$ is the same or different to $R^1$, $R^2$, $R^3$ and is selected from the group consisting of H, $CH_3$, $(CH_2)_nCH_3$ (n=1-20), $CH_2Ph$, $COCR^5R^6R^7$, CO-active esters and

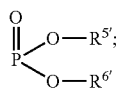

$R^{5'}$, $R^{6'}$ are the same or different and are each independently selected from the group consisting of H or a pharmaceutically suitable inorganic or organic salt, and a pharmaceutically suitable ester;

one of A and B is H, with the proviso that:

when B is H, then A is selected from the group consisting of $NHCOCH_3$, $NH_2$, OH, and $NH_2.HX$ or when A is H, B is selected from the group consisting of $NH_2$ and $NH_2.HX$, wherein HX represents a pharmaceutically suitable inorganic or organic acid; and wherein Formula (2) has the formula

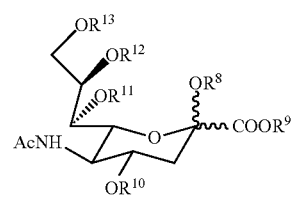

Formula (2)

wherein, $R^8$ is selected from the group consisting of H, $CH_3$, $(CH_2)_nCH_3$ (n=1-20), $CH_2Ph$, $COCH_2Ph$, CO-active ester and $COCR^{14}R^{15}R^{16}$; wherein $R^{14}$, $R^{15}$, $R^{16}$ are the same or different and are each independently selected from the group consisting of H, $CH_3$, $(CH_2)_nCH_3$ (n=1-20), $C_6H_5$, $CH_2Ph$, $CH_2CH_2(OCH_2CH_2)_mCH_3$ (m=1-200), cytidine, cytidine monophosphate, cytidine diphosphate, cytidine triphosphate, adenosine, adenosine monophosphate, adenosine diphosphate, and adenosine triphosphate;

$R^9$ is selected from the group consisting of H, $CH_3$, a pharmaceutically acceptable inorganic or organic salt, a pharmaceutically suitable active ester, and $CH_2CR^{17}R^{18}R^{19}$, wherein $R^{17}$, $R^{18}$, $R^{19}$ are the same or different and are each independently selected from the group consisting of H, $CH_3$, $(CH_2)_nCH_3$ (n=1-20), $CH_2CH_2(OCH_2CH_2)_mCH_3$ (m=1-200), $C_6H_5$, and $CH_2Ph$;

$R^{10}$, $R^{11}$, $R^{12}$ are the same or different and are each independently selected from the group consisting of H, $CH_3$, $(CH_2)_nCH_3$ (n=1-20), $CH_2Ph$, active ester, and $COCR^{20}R^{21}R^{22}$, wherein $R^{20}$, $R^{21}$, and $R^{22}$ are the same or different and are each independently selected from the group consisting of H, $CH_3$, $(CH_2)_nCH_3$ (n=1-20), $C_6H_5$, $CH_2Ph$, and $CH_2CH_2(OCH_2CH_2)_mCH_3$ (m=1-200);

$R^{13}$ is the same or different from $R^{10}$, $R^{11}$, $R^{12}$ and is selected from the group consisting of H, $CH_3$, $(CH_2)_nCH_3$ (n=1-20), $CH_2Ph$, active ester, and $COCR^{20}R^{21}R^{22}$, wherein $R^{20}$, $R^{21}$, and $R^{22}$ are the same or different and are each independently selected from the group consisting of H, $CH_3$, $(CH_2)_nCH_3$ (n=1-20), $C_6H_5$, $CH_2Ph$, $CH_2CH_2(OCH_2CH_2)_mCH_3$ (m=1-200) and

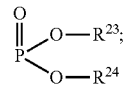

$R^{23}$, $R^{24}$ are the same or different and are each independently selected from the group consisting of H, $CH_3$, $(CH_2)_nCH_3$ (n=1-20), $CH_2CH_2(OCH_2CH_2)_mCH_3$ (m=1-200), $CH_2Ph$, or active ester, and $CH_2CR^{25}R^{26}R^{27}$, or pharmaceutically acceptable inorganic or organic salt, and $R^{25}$, $R^{26}$, $R^{27}$ are the same or different and are each independently selected from the group consisting of H, $CH_3$, $(CH_2)_nCH_3$ (n=1-20), $C_6H_5$, and $CH_2Ph$.

4. The method according to claim 3, wherein the at least one pharmaceutically acceptable compound is selected from the group consisting of N-acetylmannosamine, N-acetylneuraminic acid, CMP-sialic acid, and a pharmaceutically acceptable salt thereof.

5. The method of claim 1, wherein the pharmaceutically acceptable compound is selected from the group consisting of:
- a compound of Formula (1), in which B is H, A is $NHCOCH_3$, and each of $R^1$, $R^2$, $R^3$, and $R^4$ is H;
- a compound of Formula (2), in which each of $R^8$, $R^{10}$, $R^{11}$, $R^{12}$, and $R^{13}$ is H, and $R^9$ is Na;
- a compound of Formula (2), in which each of $R^8$, $R^{10}$, $R^{11}$, $R^{12}$, and $R^{13}$ is H, and $R^9$ is $C_2H_5$;
- a compound of Formula (2), in which $R^8$ is H, $R^9$ is $C_2H_5$, and each of $R^{10}$, $R^{11}$, $R^{12}$, and $R^{13}$ is $CH_3CO$;
- a compound of Formula (2), in which $R^8$ is cytidine monophosphate, and each of $R^9$, $R^{10}$, $R^{11}$, $R^{12}$, and $R^{13}$ is H; and
- a compound of Formula (2), in which each of $R^8$, $R^{10}$, and $R^{11}$ is H, and $R^{12}$ and $R^{13}$, together, are $C(CH_3)_2$.

6. The method of claim 3, wherein the pharmaceutically acceptable compound is selected from the group consisting of:
- a compound of Formula (1), in which B is H, A is $NHCOCH_3$, and each of $R^1$, $R^2$, $R^3$, and $R^4$ is H;
- a compound of Formula (2), in which each of $R^8$, $R^{10}$, $R^{11}$, $R^{12}$, and $R^{13}$ is H, and $R^9$ is Na;
- a compound of Formula (2), in which each of $R^8$, $R^{10}$, $R^{11}$, $R^{12}$, and $R^{13}$ is H, and $R^9$ is $C_2H_5$;
- a compound of Formula (2), in which $R^8$ is H, $R^9$ is $C_2H_5$, and each of $R^{10}$, $R^{11}$, $R^{12}$, and $R^{13}$ is $CH_3CO$;
- a compound of Formula (2), in which $R^8$ is cytidine monophosphate, and each of $R^9$, $R^{10}$, $R^{11}$, $R^{12}$, and $R^{13}$ is H; and
- a compound of Formula (2), in which each of $R^8$, $R^{10}$, and $R^{11}$ is H, and $R^{12}$ and $R^{13}$, together, are $C(CH_3)_2$.

7. The method of claim 1, wherein the at least one pharmaceutically acceptable compound is administered by inhalation.

8. The method of claim 3, wherein the at least one pharmaceutically acceptable compound is administered by inhalation.

* * * * *